Figure 1A:
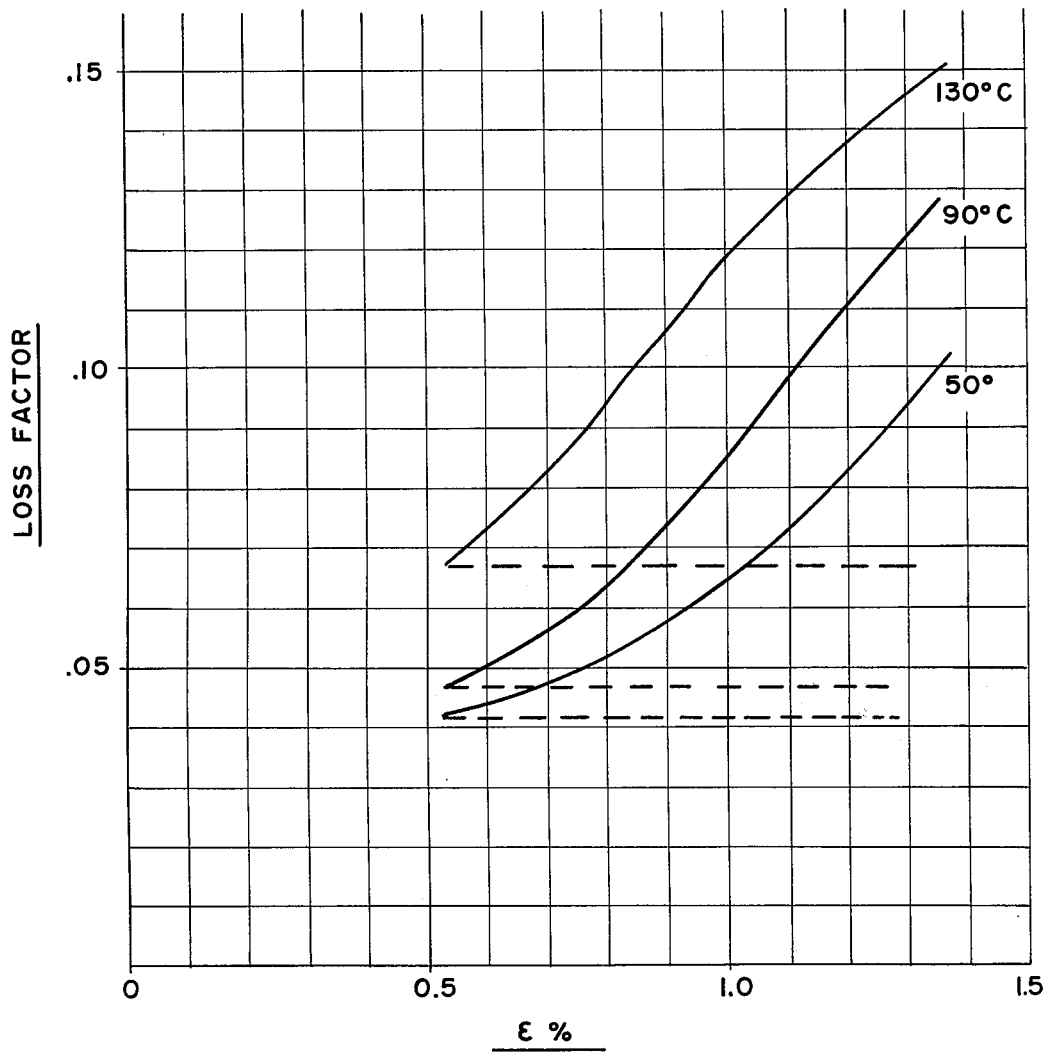
Figure 1B:
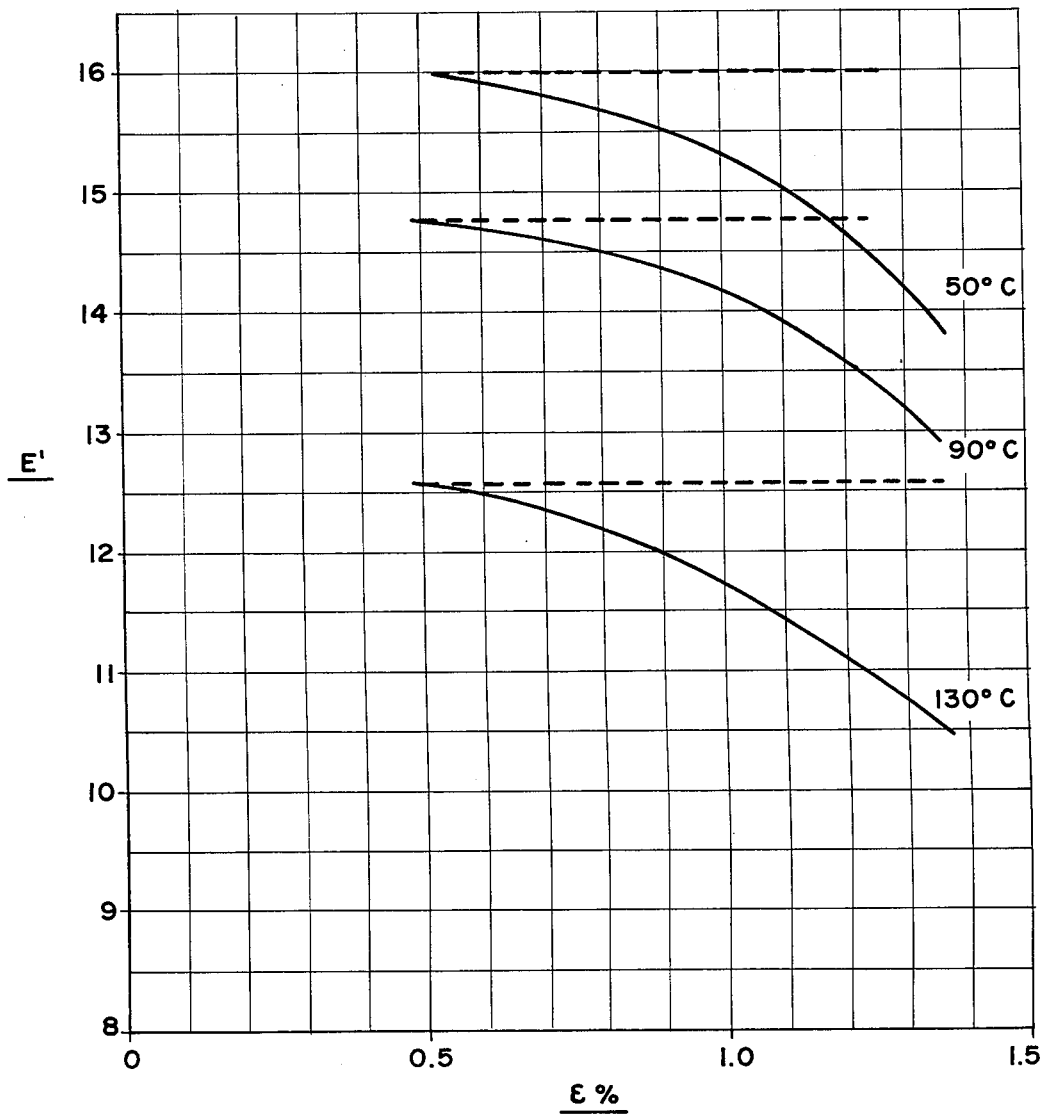

United States Patent [19]
Prevorsek et al.

[11] 3,934,452
[45] Jan. 27, 1976

[54] METHOD OF DETERMINING DYNAMIC STRAINS IN COMPOSITE STRUCTURES

[75] Inventors: Dusan Cyril Prevorsek; Young Doo Kwon; Raj Kumar Sharma, all of Morristown, N.J.

[73] Assignee: Allied Chemical Corporation, New York, N.Y.

[22] Filed: Dec. 2, 1974

[21] Appl. No.: 528,610

[52] U.S. Cl. .................. 73/15.6; 73/92; 73/146
[51] Int. Cl.² ............................................ G01N 3/32
[58] Field of Search ............... 73/15.6, 146, 92, 99

[56] References Cited
UNITED STATES PATENTS
1,680,589  8/1928  Bock .................................. 73/15.6

OTHER PUBLICATIONS
Baldwin et al., Experimental Exam. of Statistical Theory of Rubber Elasticity, Low Extension Studies, J. of Applied Phys., Vol. 26, No. 4, June, 1955.

Primary Examiner—James J. Gill
Assistant Examiner—Anthony V. Ciarlante
Attorney, Agent, or Firm—Robert A. Harman

[57] ABSTRACT

A method for determining strain amplitudes in each component, during cyclic straining of a 2-component structure in which at least one component shows nonlinear viscoelastic behavior. The heat generation rates of each component are determined experimentally, at various temperatures, as functions of the experimentally imposed strain amplitudes. These functions are used to solve, by computer, a heat balance equation involving temperature values through the structure. To find pairs of strain amplitudes which produce observed temperatures, the value of strain amplitude entering into the equations for one component is varied (for each value of a set of strain amplitudes of the other component) until the temperature at a selected point of the structure, thus calculated, matches the temperature determined experimentally; and likewise for a second selected point. The desired pair of strain amplitudes is thus identified as being a pair which produces a match of calculated vs. measured temperature at both selected points.

5 Claims, 10 Drawing Figures

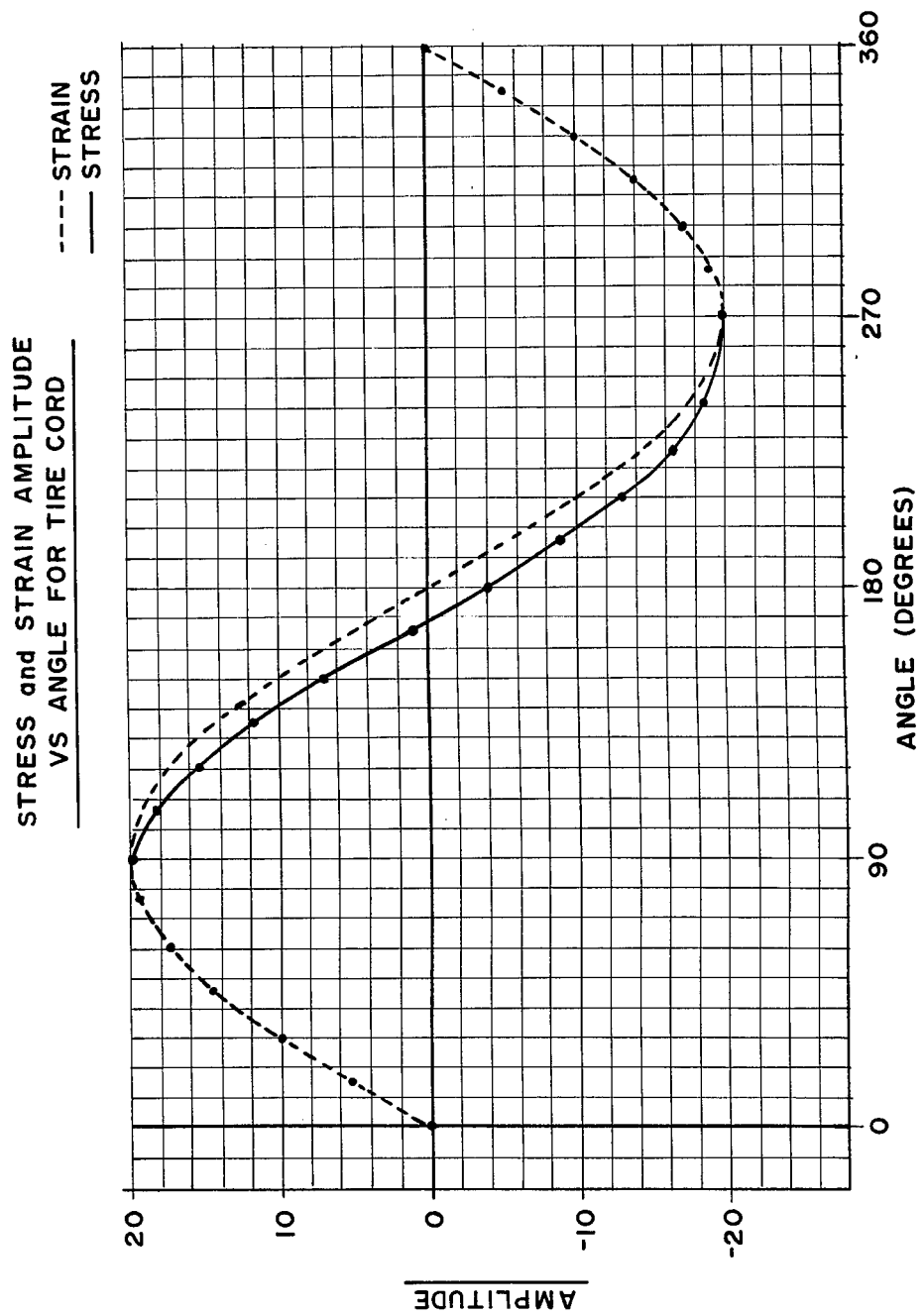

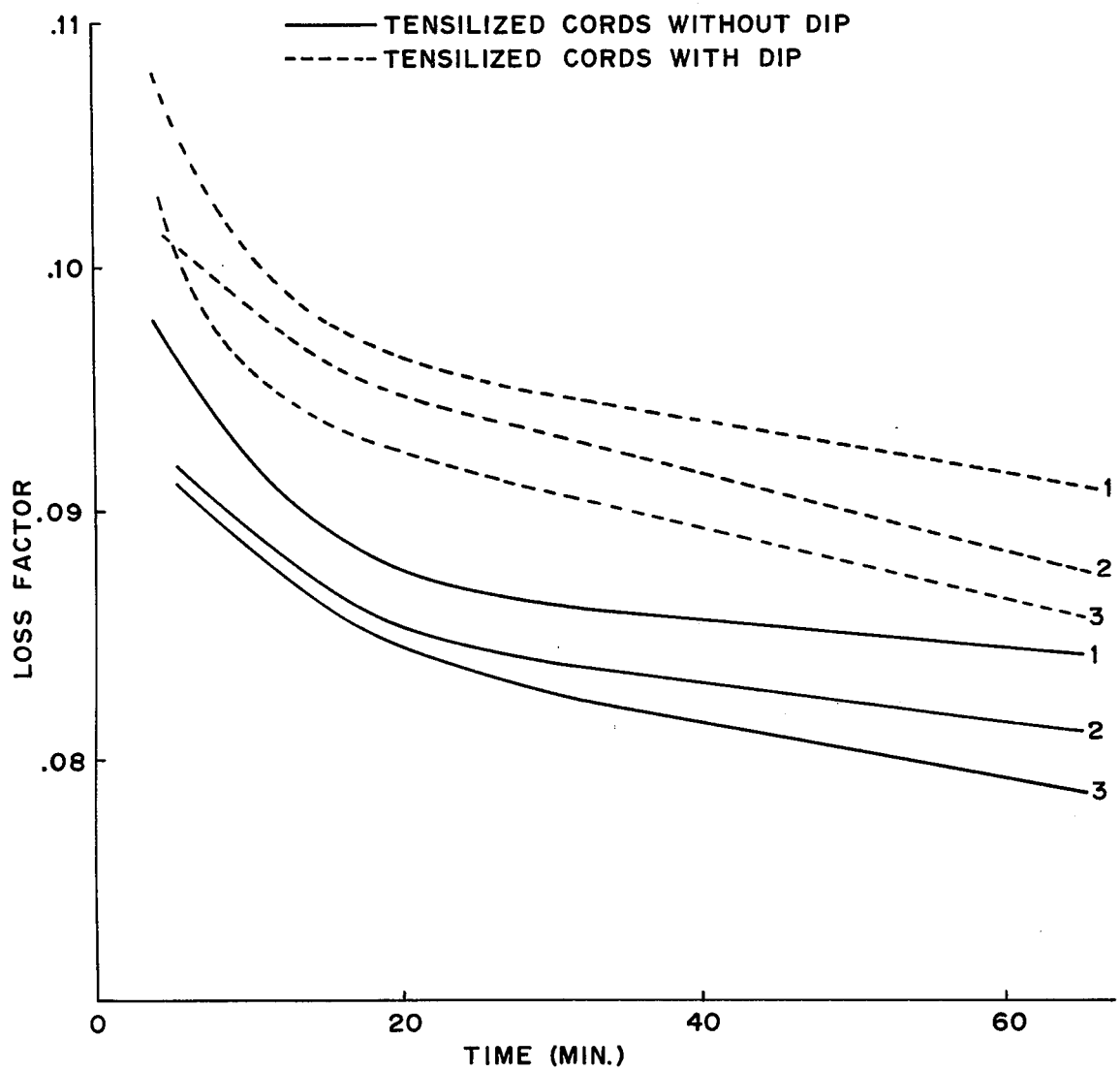
FIG. 3ᵍ

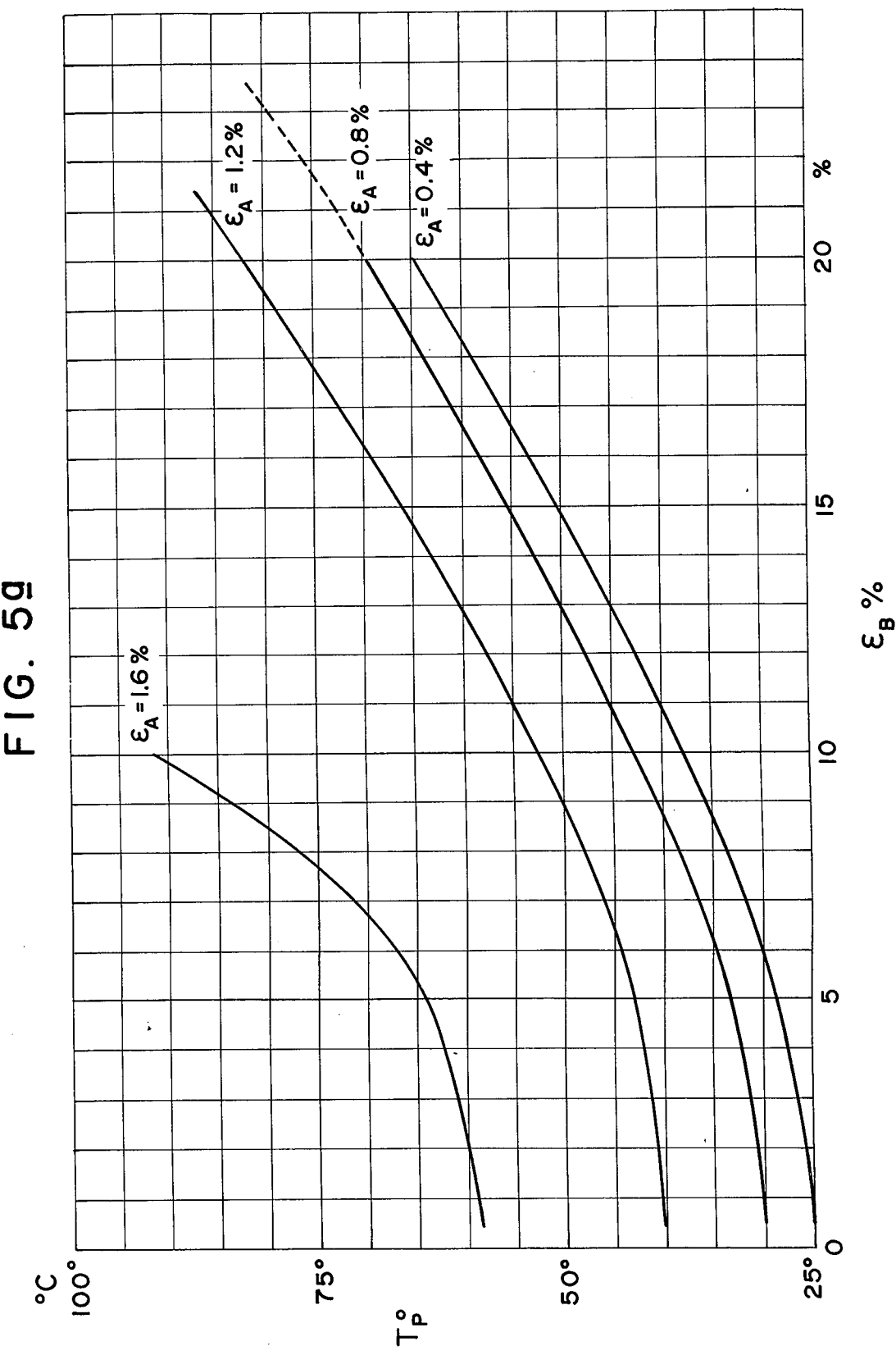

METHOD OF DETERMINING DYNAMIC STRAINS IN COMPOSITE STRUCTURES

BACKGROUND OF THE INVENTION

This invention relates to determination of strains developed by cyclic deformation of structures such as pneumatic tires.

Analysis of the tire temperature rise is reported in the published scientific and patent literature. Such analysis can be found, for example, in the following articles:

P. Kainradl, G. Kaufmann and F. Schmidt, in Kautschuk Und Gummi-Kunststoffe, vol. 19, 27, (1966), discussing the relationship between temperature rise in pneumatic tires and viscoelastic properties of rubber;

J. M. Collins, W. L. Jackson and P. S. Oubridge, "Relevance of Elastic and Loss Moduli of Tyre Components to Tyre Energy Loss", in Transactions of the Rubber Industry, vol. 40 T239 (1964).

U.S. Pat. No. 3,553,307 to F. J. Kovac and G. W. Rye, "Treatment of Polyester Tire Cord", col. 5, lines 22–54.

When such cyclic dynamic experiments are conducted using a sinusoidal alteration of stress or strain, for so-called "linear" viscoelastic solids, the instantaneous stress ($\sigma$) varies periodically with time ($t$) according to $$\sigma(t) = \epsilon_o (E' \sin \omega t + E'' \cos \omega t) \qquad (1)$$

sin ($\omega E'$ is the dynamic modulus, $E''$ is the loss modulus; $\epsilon_o$ is the strain amplitude; and $\omega$ is the frequency of cyclic straining in radians/sec. The variation of instantaneous stress with time during cyclic stressing can also be expressed for linear viscoelastic solids by means of the amplitude of the stress, $\sigma_o$, and the phase angle $\delta$ between the stress and strain:

$$\sigma(t) = \sigma_o \sin(\omega t + \delta) = \sigma_o \cos \delta \sin(\omega t) + \sigma_o \sin \delta \cos (\omega t) \qquad (2)$$

Consequently, $$E' = \frac{\sigma^o}{\epsilon_o}\cos \delta \; ; \; E'' = \frac{\sigma^o}{\epsilon_o}\sin \delta \; ; \text{ and } E''/E' = \tan \delta.$$

The important assumption in the linear viscoelastic theory is that the moduli $E'$, $E''$ and the phase angle $\delta$ are constant during the cycle.

Figure 2A:
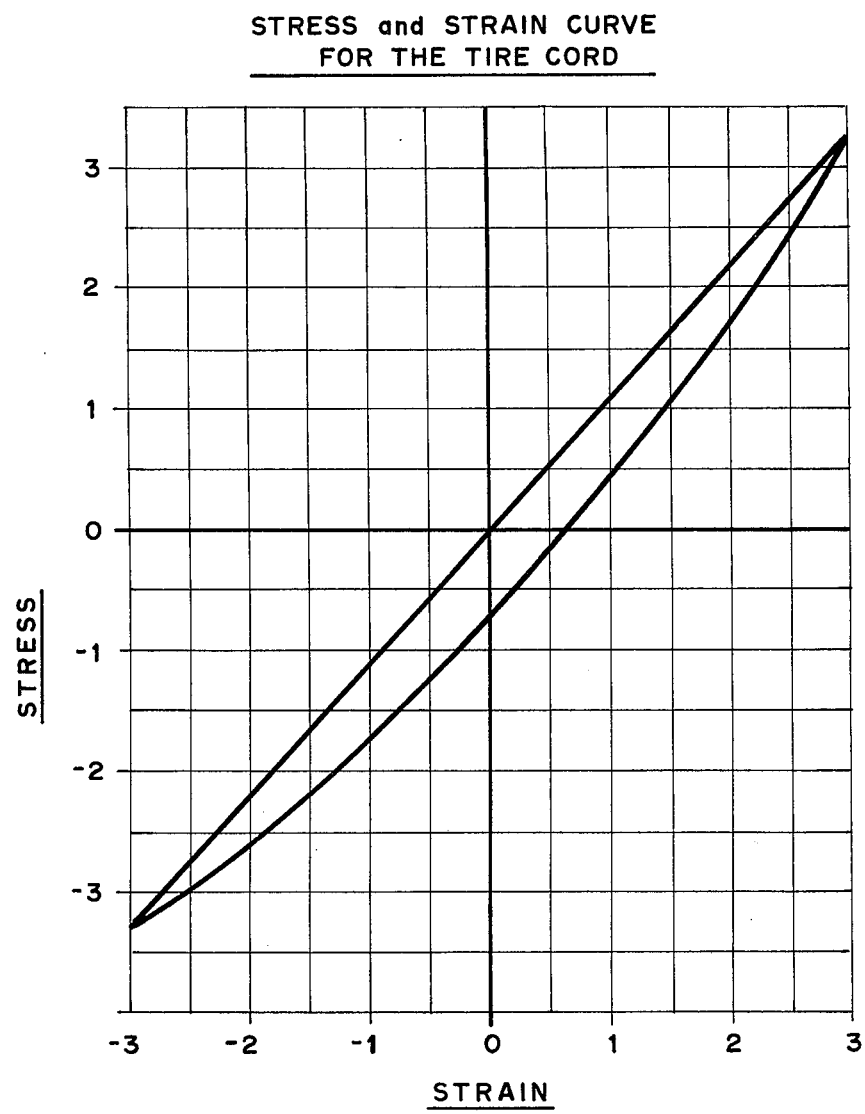
Figure 3B:
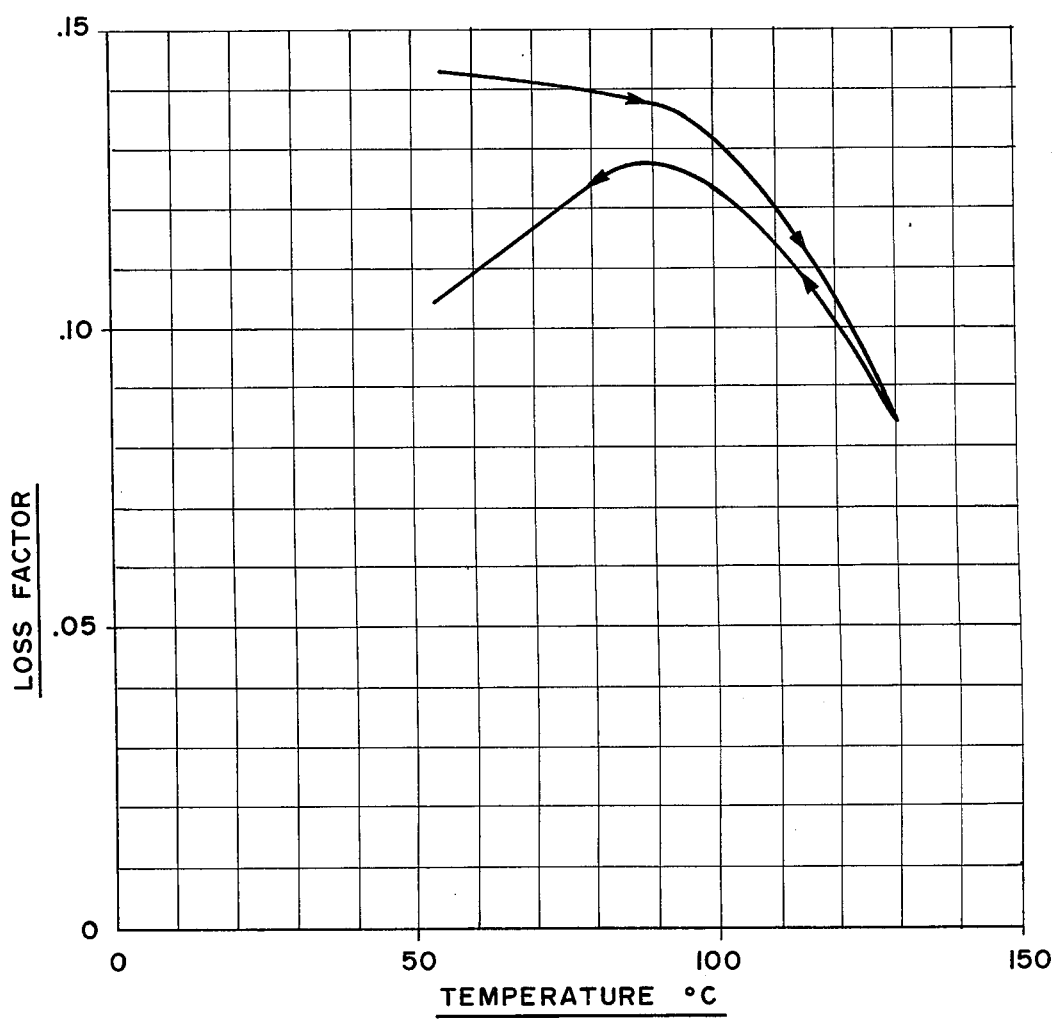
Figure 4:
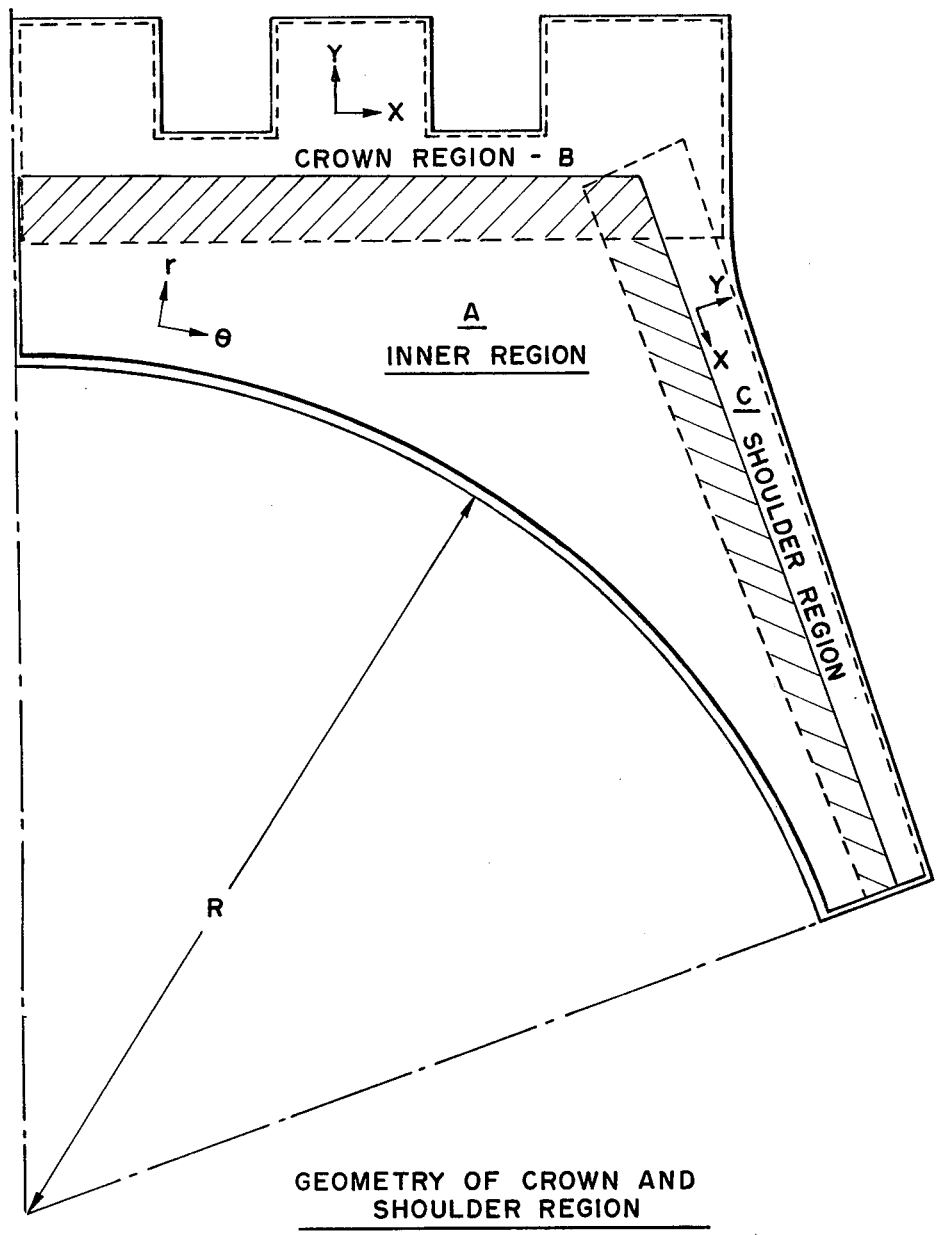

The annexed FIGS. 1(a), 1(b), 2(a), 2(b), 3(a), 3(b) are graphs described below; and FIG. 4 is a diagram of a radial cross-section of a vehicular pneumatic tire.

Figure 5B:
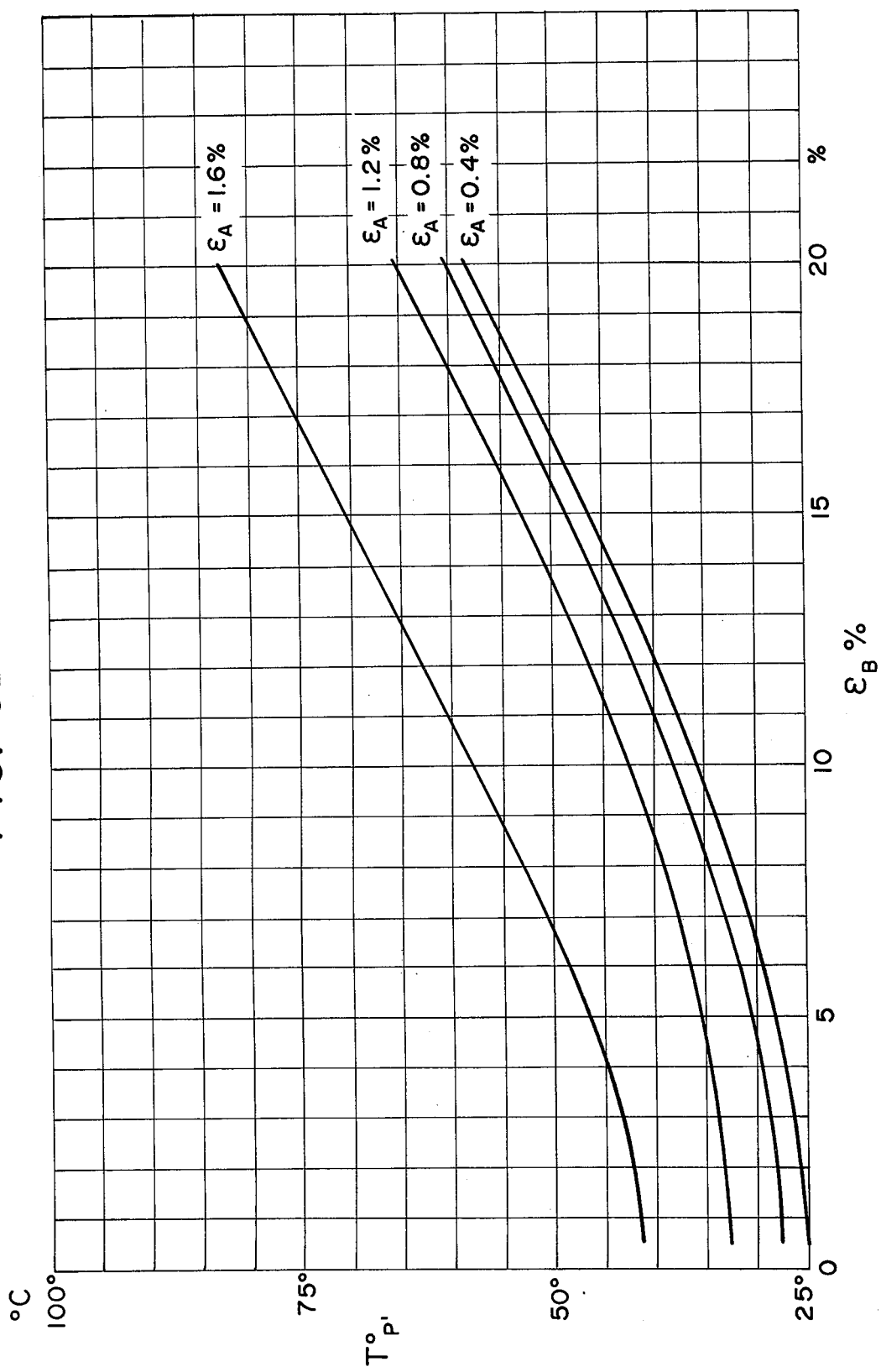
Figure 5C:
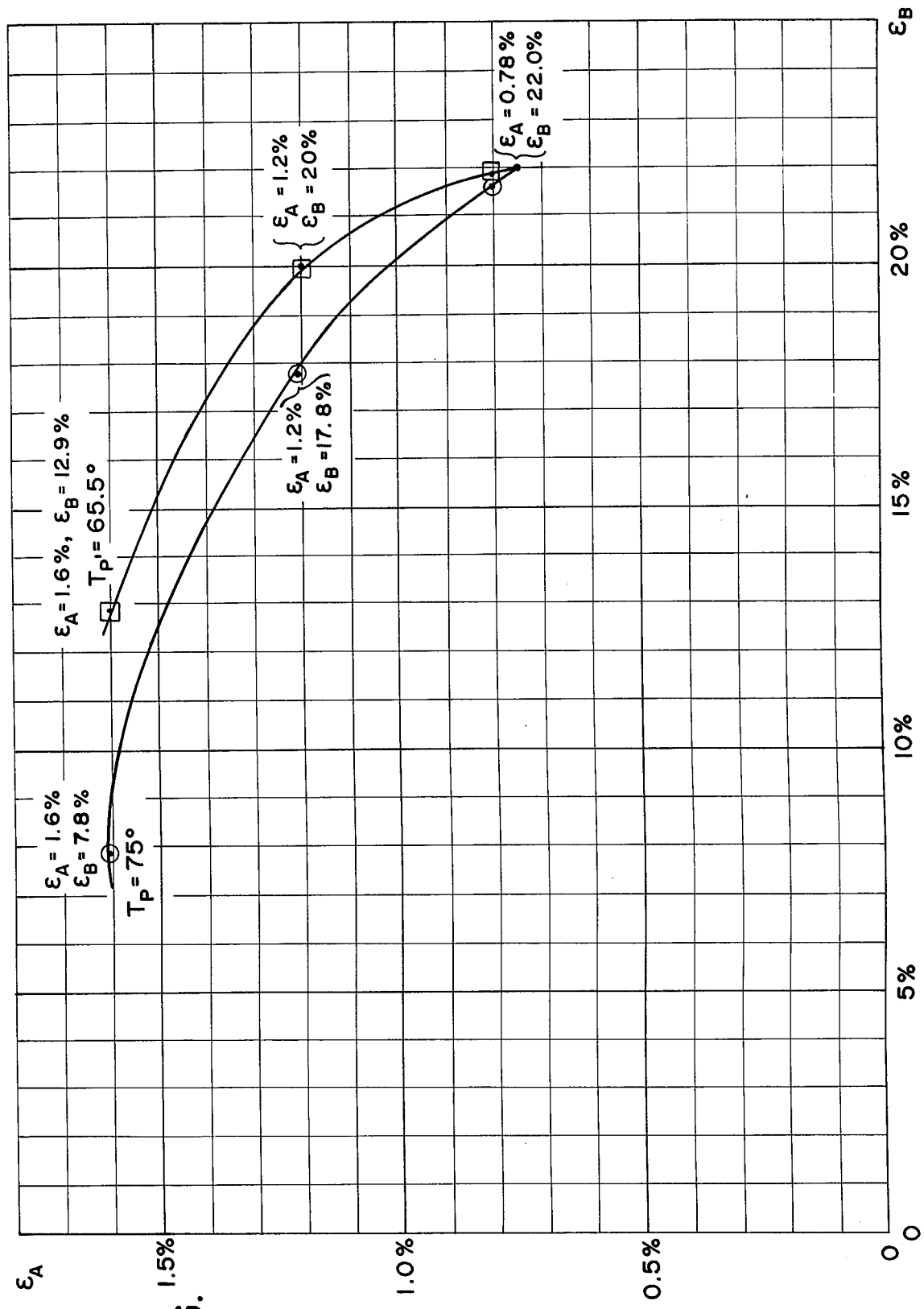

FIGS. 5(a), 5(b) and 5(c) illustrate the relationships between strains and temperatures at the center and at the wall surface of a cylindrical structure of a core material surrounded by a wall material, subjected to lengthwise cyclical straining and having strain amplitudes in the core differing from those in the wall; as more fully described in connection with Example 1 below.

The equations above approximate well the behavior of crosslinked rubbers, and glassy polymers under strain amplitudes of less than 0.1%. However, in the range of strain amplitudes of about 0.3% and greater, oriented, crystalline polymers of e.g., polyethylene terephthalate ("PET") and nylon used in tire cords exhibit behavior which in many respects significantly differs from that predicted by the linear viscoelastic theory. The magnitude of deviation, from the linear behavior, of a poly(ethylene terephthalate) cord in loss factor and dynamic modulus is illustrated in FIGS. 1(a) and (b). There, the solid lines represent the observed responses, and the dotted lines indicated the responses predicted assuming linear viscoelastic behavior. Considering that changes in loss factor or modulus which are greater than 5% usually lead to significant effects on tire performance, it can be concluded that analysis of tire temperature rise by means of linear viscoelastic equations leads to erroneous results.

Moreover, we have found that in fact the viscoelastic properties $E'$, $E''$ and tan $\delta$ vary cyclically during the cyclic straining of cords composed of oriented, crystalline polymers. This behavior is illustrated by the stress-strain cycle of a tensilized PET tire cord (denier ~ 3500) subjected to a cyclic strain amplitude of 1.14% at a null point tension (i.e., average tension or "pretension") of 5 Kg and at temperatures of 120°C. and frequency of 10 cps (cycles per second) as shown in FIG. 2(a).

From the data of FIG. 2(a) we constructed a composite plot showing the variation of instantaneous strain and instantaneous stress each as function of time during the cycle, in particular as function of the angles ($\omega t$) and ($\omega t + \delta$), of cyclic straining as shown along the hysteresis loop of FIG. 2(a). This is shown in FIG. 2(b).

The results of FIG. 2(b) show that the phase difference between the stress and strain is negligible during the elongating phases of the cycle, i.e., between 0°–90° and 270°–360°; and large during the contraction phase, between 90° and 270°. In other words, the phase angle $\delta$ is a function of the angle of the cyclic strain. For a solid, such as crosslinked rubber, approximating linear viscoelastic behavior, on the other hand, the phase angle between the stress and strain is independent of the strain amplitude angle during the cycle.

On the basis of these results we concluded that the rate of heat generation for tire cords cannot be determined using tan $\delta$ and $E''$ as mentioned in the publications cited above. In fact, because phase angle $\delta$ is not constant over the cycle, $\delta$ has no physical meaning for tire cord behavior in the sense used in linear viscoelastic behavior.

Finally, it must be recognized that under conditions of pretension, strain (or stress) amplitude, and temperature such as encountered in tires, the viscoelastic properties of cords depend on time, temperature and stress history, as seen in FIGS. 3(a) and (b). In FIG. 3(a) is shown the plot of loss factor as function of time for a PET cord at a pretension of 1.2 g/denier and a frequency of 10 cps (cycles per second) in a dynamic experiment. The cord pretensions and strain amplitude are constant. (Loss factor is defined as ratio of energy lost as heat per cycle: energy input per cycle during cyclic deformation.) FIG. 3(b) shows the plot of loss factor of a nylon cord at 1.2 g/denier pretension and 10 cps frequency during the heating and cooling cycle in a temperature range encountered in bias and bias belted tires. The experiment started at 50°C. There is seen to be a large difference between the loss factor at 50°C. at the beginning vs. that at the end of the experiment. These results show that in order to carry out the tire self-heating and tire deformation analysis observed below, the cords must be subjected to conditioning treatments consisting of cyclic deformation, similar to that operating in tires during testing, continued long enough so that consistent results for heat loss are obtained in subsequent testing.

With accumulated data regarding the viscoelastic responses of tire cords it becomes possible to use tire temperature data to determine the cord and rubber strain amplitudes in tires as the tires are rolling, from temperature measurements. This is an important aspect of this invention.

The most frequently used method to measure stresses and strains in deformed articles involves incorporation of stress and strain transducers on the surface or in the body of the specimen. These techniques become very involved when applied to specimens consisting of several types of materials (composites) because the stress (strain) measuring devices must be placed in all components of the composite specimen. A very important class of composites are those in which a low modulus and low strength matrix is reinforced with high modulus, high strength material in filament, yarn or cord form. The determination of filament or cord stresses in the reinforced zone of such composites requires specially designed stress (strain) measuring devices which must be incorporated into the reinforced zone. This operation cannot be carried out without severe distortion of structure which may severely affect the deformation of the reinforcing composite in the vicinity of the measuring device. An important advantage of our invention is that it provides a method to determine the stress (strain) amplitude of the components within a composite structure during periodic deformation without implanting stress (strain) sensors in the reinforced zone thereof.

EXAMPLE A

This example illustrates methods used in accordance with this invention to determine relation between cyclic strain amplitude and observed temperature rise in a composite structure, occurring during a dynamic viscoelastic experiment. The particular structure consists of a cylindrical core of a material A and an outer wall of material B. The diameter of the core equals the inner diameter of the outer wall. In the preparation of the composite, a thin layer of adhesive is applied to the surface of the core to ensure good adhesion of the core to the outer wall.

By use of apparatus for lengthwise cyclically straining viscoelastic specimens and recording the instantaneous stress and strain, we determined at various strain amplitudes and at various temperatures the heat generation rate (defined as area within the closed loop of a cyclic stress-strain plot, as in FIG. 2(a) multiplied by frequency) for a material A, a uniaxially oriented PET monofil having a diameter D=0.076 cm; and B, s cross-linked rubber tube having inner diameter D=0.076 cm and wall thickness W=0.152 cm. The values for the PET monofil were found for strain amplitudes of 0.61, 0.89 and 1.15%. Since rubber is a linear viscoelastic solid, a single curve applies for all strain amplitudes thereof in the range of 0.4–1.5%. The tests were at temperatures of 50°, 70°, 90°, 105°, 120°, 135°, 150° and 160°C.

Then the composite specimen is subjected to strain amplitudes (in tension) of 0.4, 0.8 and 1.5% at frequencies of 10, 20 and 50 cps. The clamping of the specimen is such that both the core and the outer wall are subjected to the same strain amplitude. After the specimen reaches the steady state temperature conditions (in about 60 min.), the specimen surface temperature ($T_S$) and the temperature ($T_B$) at the boundary between the core and the outer wall are recorded.

The temperature profile across the specimen is determined by solving by computer the equation:*

(for the derivation of such heat balance equation, see, for example, Chapter 10, of Bird et al., "Transport Phenomena", J. Wiley, New York, 1960.)

$$\rho C_p \frac{\partial T}{\partial t} = \frac{1}{r} \frac{\partial}{\partial r}\left(rK \frac{\partial T}{\partial r}\right) + Q$$

$\rho$ = density of PET or rubber as applicable
Cp = heat capacity of PET or rubber as applicable
$T$ = temperature
$t$ = time
$r$ = radial coordinate
$K$ = thermal conducivity (PET or rubber as applicable)
$Q$ = heat generation rate for cord or for rubber as applicable, when at the calculated temperature and subjected to a given strain amplitude;

under the following boundary conditions:

1. At $r = 0$
$\partial T/\partial r = 0$.

2. At $r = D/2$, $$K \left(\frac{\partial T}{\partial r}\right)_P = K \left(\frac{\partial T}{\partial r}\right)_R$$

where D is core diameter and the subscripts P and R refer to the PET polymer and to the rubber regions, respectively.

3. At $r = D/2 + W$, $$-K \left(\frac{\partial T}{\partial r}\right)_R = h(T-T_a)$$

where
$h$ = heat transfer coefficient, rubber to air
$T_a$ = ambient air temperature
$W$ = wall thickness of rubber tube.

Digital computer determination of the temperature profile involves the numerical solution of the above heat transfer equation through the use of finite difference approximation technique.

A set of simultaneous equations in $T_i$ and $Q_i$, one equation for each small volume element of the composite and for each successive small time interval is constructed assuming heat flow only along the radial dimension of the composite. The equations are solved by a general purpose digital computer, initially inserting unknown temperatures, $T_i$, for each successive small volume interval through the structure and using the ambient temperature, $T_a$, as the temperature at the preceding small time interval, so that the initial ($\partial T/\partial t$) is approximated at the $i^{th}$ volume element by $(T_i-T_a)/\Delta t$; ($\partial T/\partial r$) by $(T_{i+1}-T_i)/\Delta r$; and ($\partial^2 T/\partial r^2$) by $(T_{i+1}-2T_i+T_{i-1})/(\Delta r)^2$. An initial set of $T_i$ is thus calculated; and the calculation is then repeated using these $T_i$'s for each volume element, instead of $T_a$, to approximate ($\partial T/\partial t$). The values to be taken for $Q_i$ in each equation, at each calculated temperature $T_i$, are derived from the experimentally determined values for heat generation rates at the various temperatures and at the various strain amplitudes above mentioned.

Polynomial expressions in ($\epsilon$) (where $\epsilon$ represents the strain amplitude) are used to represent the various experimental heat generation rates as measured at various levels of temperature.

A value of ($\epsilon$) is chosen, approximately the experimental value, for input to the computer. The computer solution using this value generates a radial temperature profile.

The values of $Q_i$ are then updated for the updated temperature at each volume element, proceeding as follows: The experimentally established polynomial expressions in ($\epsilon$) are used to compute the experimental values of $Q_i$ for the nearest higher and lower temperature; then $Q_i$ at the intermediate temperature of interest is approximated by linear interpolation between these two experimental $Q_i$ values; all being done by computer. Eventually this process generates a steady state radial profile of temperature.

The resulting steady state temperature values are compared with the experimentally recorded values of $T_S$ (surface temperature) and $T_B$ (temperature at the boundary between core and wall). Small changes in ($\epsilon$) are then made until finally the calculated steady state values and the experimental values of temperature match closely. The value of ($\epsilon$) which was used in obtaining this last computer solution represents the strain which occurred in the experiment; and the final values of $T_i$ thus obtained represent the steady state tempera-

| Symbol | Definition | Units | Value |
|---|---|---|---|
| | PET density | g/cc | 1.38 |
| $\rho$ | rubber density | g/cc | 1.15 |
| $C_p$ | PET heat capacity | cal/g/°C | 0.343 |
| | rubber heat capacity | | 0.357 |
| K | PET thermal conductivity | cal./cm sec °C | $6.5 \times 10^{-4}$ |
| | rubber thermal conductivity | " | $6.8 \times 10^{-4}$ |
| h | heat transfer coefficient | cal./cm² sec °C | $5.0 \times 10^{-4}$ |
| $T_a$ | ambient air temperature | °C | 25.0 |

The calculated temperatures are listed in the table which follows. If actual temperature values have been recorded, a close match can be obtained by adjusting $\epsilon$ in the polynomial for each $Q_i$ as above described, until an effective value of $\epsilon$ is found which may differ somewhat from the experimental value. In the table below, the recorded temperatures at 20 cps were arbitrarily set at reasonable values and were then closely matched by interpolating on the computer, making small changes in $\epsilon$, until such effective value of strain amplitude, $\epsilon_{eff}$, had been determined. Calculated values of temperature can then be established for the other frequencies using this same $\epsilon_{eff}$, and will closely approximate recorded temperatures as indicated in Table I which follows.

TABLE I

"RECORDED" TEMPERATURES (°C.) vs. CALCULATED STEADY STATE TEMPERATURES OF CYLINDRICAL COMPOSITE DURING CYCLIC STRESSING

| Frequency cps | Cyclic Strain Amplitude, % | $T_c$ (at center) Calc. | $T_B$ (at core/wall boundary) | | $T_s$ (at surface) | |
|---|---|---|---|---|---|---|
| | | | Calc. | Recorded | Calc. | Recorded |
| 10 | 0.4 | 25.07 | 25.02 | — | 25.01 | — |
| | 0.8 | 27.13 | 26.40 | — | 26.61 | — |
| | 1.5 | 36.13 | 34.95 | 35.0 | 34.44 | 33.5 |
| 20 | 0.4 | 25.04 | 25.04 | — | 25.02 | — |
| | 0.8 | 29.24 | 28.72 | — | 28.21 | — |
| | 1.5 | 47.17 | 44.82 | 45.0 | 41.81 | 42.0 |
| 30 | 0.4 | 25.11 | 25.10 | — | 25.08 | — |
| | 0.8 | 35.58 | 34.45 | — | 33.02 | — |
| | 1.5 | 127.21 | 116.62 | 116.0 | 102.72 | 103.0 |

$D_{core} = 0.076$ cm
Wall thickness = 0.152 cm ture profile radially through the composite (at relatively large distance from the ends) when the composite is subjected to cyclic straining at the strain amplitude so determined and at the specified frequency, tension and ambient temperature.

When temperatures of the composite are known, it is evident that the strain applied thereto can be determined by interpolation between values given in Table I below.

The following values of physical parameters were used in this example for solving the above heat transfer equation:

EXAMPLE B

This example illustrates that it is possible to predict by the above method, using data for a given specimen, the temperature rise for other specimens having like structure but different dimensions.

This second specimen has a core diameter $D = 0.152$ cm and wall thickness $W = 0.304$ cm. The experimental heat generation rates at various temperatures, used in this example, and also the effective value of $\epsilon$ were those used in Example A above. Under the conditions of strain amplitude and frequency listed below in Table II, we obtain the set of temperature data summarized in Table II.

TABLE II

COMPARISON OF TYPICAL RECORDED TEMPERATURES (°C.) OF CYLINDRICAL COMPOSITE DURING CYCLIC STRESSING

| Frequency cps | Cyclic Strain Amplitude, % | $T_c$ (at center) Calc. | $T_B$ (at core/wall boundary) | | $T_s$ (at surface) | |
|---|---|---|---|---|---|---|
| | | | Calc. | Recorded | Calc. | Recorded |
| 10 | 0.4 | 25.07 | 25.06 | — | 25.04 | — |
| | 0.8 | 30.30 | 29.40 | — | 28.25 | — |
| | 1.5 | 53.24 | 48.40 | 48.5 | 42.26 | 42.0 |
| 20 | 0.4 | 25.12 | 25.10 | — | 25.08 | — |
| | 0.8 | 35.55 | 33.75 | — | 31.45 | — |
| | 1.5 | 128.31 | 111.28 | 112.0 | 88.56 | 89.0 |
| 50 | 0.4 | 25.29 | 25.24 | — | 25.18 | — |

TABLE II-continued
COMPARISON OF TYPICAL RECORDED TEMPERATURES (°C.) OF CYLINDRICAL COMPOSITE DURING CYCLIC STRESSING

| Frequency cps | Cyclic Strain Amplitude, % | $T_c$ (at center) Calc. | $T_B$ (at core/wall boundary) Calc. | $T_B$ Recorded | $T_s$ (at surface) Calc. | $T_s$ Recorded |
|---|---|---|---|---|---|---|
| | 0.8 | 51.34 | 46.84 | — | 41.09 | — |
| | 1.5 | 172.61 | 147.41 | 148.0 | 115.11 | 115.5 |

$D_{Core} = 0.152$ cm
Wall thickness = 0.304 cm

EXAMPLE I

This example illustrates our invention applied to a two-phase cylindrical composite like those of Examples A and B above, in which the strain amplitude in one phase differs from that in the other phase. This example shows that the strain amplitudes of the two phases can be determined uniquely if the steady state temperatures at two locations in the composite are known.

The experimental heat generation and the physical parameters used are those used in Example A above. Diameter of the core: D = 0.32 cm; thickness of the wall: W = 0.48 cm; frequency of cyclic stressing = 10 cps.

In this example, four different combinations of temperatures ($T_c$, $T_s$) are taken as representing typical specimen core temperatures at the center ($T_c$) and wall surface temperatures ($T_s$) as listed in the table below:

| | $T_c$ | $T_s$ |
|---|---|---|
| (A) | 75° | 60° |
| (B) | 75° | 65.5° |
| (C) | 82° | 60° |
| (D) | 82° | 65.5° |

In order to determine the strain amplitudes, $\epsilon_c$ and $\epsilon_w$ which would lead at steady state temperature conditions to the pairs of temperatures ($T_c$, $T_s$) listed above, we proceed as follows:

1. The rates of heat generation ($Q_c$) and ($Q_w$) per unit volume of core material and wall material, respectively, due to cyclic stressing, are experimentally determined on a sample of each material at a series of temperatures, by hysteresis measurements at various strain amplitudes ($\epsilon_c$) for core material and ($\epsilon_w$) for wall material:

2. For each pair of a set of pairs of strain amplitudes, ($\epsilon_c$, $\epsilon$), finite difference approximations — at successive positions through the whole structure and successive time intervals are constructed to solve by computer for the temperatures in the heat balance differential equation appropriate for a cylindrical structure, using the procedure and values of parameters shown in Example A above. The required heat generation rates per unit volume are found by expressing $Q_c$ and $Q_w$ as polynomials in $\epsilon_c$ and $\epsilon_w$, respectivley, at the temperature calculated for each volume element dV, and inserting the given values of the strain amplitude pairs ($\epsilon_c$, $\epsilon_w$).

The results of these calculations are tabulated in the table below:

TABLE III

Calculated steady state temperatures of the two-phase composition as function of the core and wall strain ($\epsilon_c$ and $\epsilon_w$). Frequency = 10 cps.

| $\epsilon_c$ % | $\epsilon_w$ % | $T_c$ °C. | $T_s$ °C. |
|---|---|---|---|
| 0.4 | 0.5 | 25.084 | 25.052 |
| | 1 | 25.190 | 25.142 |
| | 5 | 28.515 | 27.934 |
| | 10 | 37.900 | 35.823 |
| | 20 | 64.806 | 58.487 |
| | 50 | 151.851 | 131.623 |
| | 100 | 221.697 | 192.911 |
| 0.8 | 0.5 | 30.037 | 37.486 |
| | 1 | 30.141 | 27.573 |
| | 5 | 33.138 | 30.301 |
| | 10 | 42.548 | 38.004 |
| | 20 | 69.324 | 60.350 |
| | 50 | 155.465 | 132.816 |
| | 100 | 223.888 | 193.236 |
| 1.2 | 0.5 | 40.151 | 32.455 |
| | 1 | 40.250 | 32.583 |
| | 5 | 42.583 | 35.132 |
| | 10 | 52.299 | 42.540 |
| | 20 | 81.770 | 65.471 |
| | 50 | 161.614 | 134.842 |
| | 100 | 228.573 | 193.932 |
| 1.6 | 0.5 | 58.531 | 41.441 |
| | 1 | 58.697 | 45.554 |
| | 5 | 63.796 | 45.023 |
| | 10 | 86.020 | 58.279 |
| | 20 | 121.245 | 82.878 |
| | 50 | 173.160 | 138.648 |
| | 100 | 236.789 | 195.152 |

3. Using the data of the above table, we represent the steady-state $T_c$ and the steady state $T_s$ each as a function of $\epsilon_c$, for each $\epsilon_w$ of the series of $\epsilon_w$'s; and each also as a function of $\epsilon_w$, for the series of $\epsilon_c$'s.

4. Using the resulting data, we represent $\epsilon_c$ versus $\epsilon_w$ for one of the recorded values of $T_c$, viz., $T_c = 75°$ or 82° and for one of the recorded values of $T_s$ (60° or 65.5°).

5. We determine the point of intersection of the curve ($\epsilon_c$ vs. $\epsilon_w$) for a given $T_c$, with the $\epsilon_c$ vs. $\epsilon_w$ curve for a given $T_s$. The coordinates of such point are a pair of strain amplitudes ($\epsilon_c$, $\epsilon_w$). Since there is only one such point of intersection found for each pair of temperatures, its coordinates are indicated to be the correct values of the strain amplitudes in core and wall for each pair ($T_c$, $T_s$) of temperatures examined.

The points of intersection thus determined for each of the above recorded temperature pairs ($T_c$, $T_s$) give the following values for the strain amplitudes ($\epsilon_c$, $\epsilon_w$) at the recorded temperatures:

| | ($T_c$,$T_s$) | $\epsilon_c$ (%) | $\epsilon_w$ (%) |
|---|---|---|---|
| (A) | 75°, 60° | 1.26 | 17.6 |
| (B) | 75°, 65.5° | 0.78 | 22.0 |
| (C) | 82°, 60° | 1.55 | 12.5 |
| (D) | 82°, 65.5° | 1.20 | 20.0 |

FIGS. 5(a), 5(b) and 5(c) illustrate by graphs the relationships involved in steps (3), (4) and (5) above in this Example I. In the figures, for the sake of generality, $\epsilon_C$ is represented by $\epsilon_A$; $\epsilon_w$ is represented by $\epsilon_B$, $T_C$ is represented by $T_P$ and $T_s$ is represented by $T_p$.

In FIG. 5(a), data from Table III above are plotted for $\epsilon_c$ = 0.4, 0.8, 1.2 and 1.6%. Values of $\epsilon_w$ are the abscissae (designated $\epsilon_B$ in the figure) and corresponding values of $T_c$ in Table III are the ordinates (designated $T_p$ in the figure).

FIG. s(b) is similarly constructed from the data of Table III, except that the ordinates are the tabulated values of $T_S$ (designated $T_p$ in the figure).

FIG. 5(c) is constructed by plotting as abscissae the values of $\epsilon_B$ (as read from FIG. 5(a)) at each intersection of a curve of FIG. 5(a) with the 75° horizontal coordinate; and plotting as ordinates the value of $\epsilon_A$ along such curve. For example one data point in FIG. 5(C) is the circled point at $\epsilon_B$ = 7.8% $\epsilon_A$ = 1.6% on the curve marked $T_p$ = 75°. A second curve in FIG. 5(c) is for $T_p$ = 65.5° and passes through the points ($\epsilon_B$ = 12.9%, $\epsilon_A$ = 1.6%), ($\epsilon_B$ = 20%, $\epsilon_A$ = 1.2%), and ($\epsilon_B$ = 21.8%, $\epsilon_A$ = 0.8%). These points are marked by squares in FIG. 5(C). The intersection of these two curves in FIG. 5(c) is at ($\epsilon_B$ = 22.0%, $\epsilon_A$ = 0.78%); which point accordingly represents the values of the strain amplitude in the wall of the cylindrical composite and in the core thereof, such that the temperature reached at the surface will be 65.5°C. and simultaneously the temperature reached in the core will be 75°C. when the structure is cyclically strained at room temperature and a rate of 10 cycles per second for a time sufficient to establish steady temperatures. These results are shown as item (B) of the above tabulation of results in this Example I.

The other tabulated results (A), (C) and (D) above are obtained similarly to (B).

EXAMPLE II

This example illustrates our invention applied to determine interply shear strain in the sidewall of a vehicular pneumatic tire. Because more than one pair of strain amplitudes is found to give a match between calculated and measured temperatures at the inner and outer walls of the tire sidewall, two tires each having a different heat generation rate for its rubber component are analyzed. It is found that one pair of elongation values, i.e., one combination of strain amplitude with shear strain rubber between reinforced plies is unique in giving the match for both tires; indicating the value of this pair to be the correct value.

The procedure is generally as in Example I, for a flat wall structure with a cord-reinforced zone between inner and outer rubber layers. The heat flow is assumed to be normal to the side wall surface.

The heat balance equation used is of the form
$\rho C_p (\partial T/\partial t) = K(\partial^2 T/\partial x^2) + Q_c v_c + Q_R(1-V_c)$,
where the symbols have the meanings shown in Example A, $x$ is the thickness dimension, and $c$ and $R$ refer to cord and rubber respectively; $V_c$ stands for the volume fraction of cord material.

The calculation is by finite difference approximation on a computer, as follows: $(\partial T/\partial t) \approx (T_i - T_i^*)/\Delta t$ where $T_i$ is temperature at a given point and $T_i^*$ is temperature at the same point at the next preceding time, each time interval being ($\Delta t$). Also $(\partial^2 T/\partial x^2) \approx (T_{i+1} - 2T_i + T_{i-1})/(\Delta x)^2$ where i−1, i, i+1 designate successive points along the thickness dimension of the side wall, with interval between them of ($\Delta x$).

The boundary conditions are:

At $x$=0, $K_R (\partial T/\partial x)_R - h(T_o - T_a)$, where $T_a$ is the temperature of air inside the tire at the time under consideration, $T_o$ is the temperature at the inside surface of the tire (where $x$ =0) and $h$ is the heat transfer coefficient of rubber to air.

At $x$=$b$ and $x$=$b_1$, $K_R (\partial T/\partial x)_R = K_m (\partial T/\partial x)_m$, where $x$=$b$ is at the inner border between rubber and composite zones, $x$=$b_1$ is outer border between these zones, and R and m refer to the rubber and the composite zones, respectively.

At $x$=$s$, $K_R (\partial T/\partial x)_R = -h(T_s - T_a)$, where $T_s$ is the temperature at the outside surface of the tire (where $x$=$s$), $T_a$ is the temperature of the ambient air, and the other symbols have their previous meaning.

The initial conditions at all points are taken as $T=T_a$, where $T_a$ = 25°C.

The required values of physical properties, entering into the equation to be evaluated are as follows:

PHYSICAL PROPERTIES OF TIRE MATERIAL

| Symbol | Description | Values |
|---|---|---|
| $\rho$ | density of core material, $\rho c$ | 1.39 gm/cc |
| | density of rubber, $\rho R$ | 11.15 gm/cc |
| $C_p$ | specific heat capacity of cord, $C_c$ | 0.343 cal/gm°C. |
| | Specific heat capacity of rubber, $C_R$ | 0.357 cal/gm°C. |
| K | thermal conductivity of cord, $K_r$ | 6.49×10⁻⁴ cal/cm-sec/°C. |
| | thermal conductivity of rubber, $K_R$ | 6.80×10⁻⁴ cal/cm-sec/°C. |
| b | thickness of inner rubber layer | 0.12 cm |
| $b_1$−b | thickness of composite zone | 0.13 cm |
| s−$b_1$ | thickness of outer rubber layer | 0.44 cm |
| $V_c$ | cord vol. frc. in composite zone | 0.334 |
| h | surface heat transfer coefficient, rubber to air | 5.5×10⁻⁴ cal/cm²-sec/°C. |

REINFORCED COMPOSITE PROPERTIES

| | | |
|---|---|---|
| $\rho_m$ = | $V_c \rho_c + (1-V_c)\rho_R$ | = 1.228 gm/cc |
| $C_m$ = | $W_c C_c + (1-W_c)C_R$ | = 0.3524 cal/gm°C. |
| $W_c$ = | $V_c \rho_c/[V_c\rho_c + (1-V_c)\rho_R]$ | = 0.336 |
| $K_m$ = | $V_c K_c + (1-V_c)K_R$ | = 6.697×10⁻⁴ cal/cm.-sec/°C. |

Subscripts:
c = cord;
R = rubber;
m = reinforced composite.

The heat generation rates per unit volume of cord and rubber stock from these tires at various elongations and temperatures were determined by the previously described procedure, choosing average tension and cycling frequency to correspond to inflation pressure and speed of the tires subjected to testing. (The relation between average cord tension and inflation pressure depends on properties of the cord and on tire construction; and may be calculated from the construction geometry or estimated from a few tests using implanted transducers; and thereafter corrected to obtain best fit of measured temperatures vs. temperatures calculated as in our herein described method.)

In each tire, the strain amplitude of rubber in the reinforced zone (plies of cord embedded in rubber), and that of the outer layer of rubber, is taken as an approximation to be equal to the strain amplitude of cords in the cord/rubber plies. Five values of cord strain amplitude in the range of 0.6 to 1.4% are each combined with several values of shear strain for the rubber layers separating the cord/rubber plies (interply rubber), to establish strain amplitude-shear strain combinations which give a best match between the calculated temperatures and measured tire temperatures. In the calculation the heat flow is assumed to be only along the thickness dimension of the sidewall and tire side wall is assumed to be a flat slab in its geometry, when the above equations are used.

Two tires are tested under identical conditions and have identical construction except for the nature of the rubber stock used. The two rubber stocks have the same modulus but the heat generation rate of rubber stock B in tire B is three times the heat generation rate of rubber stock A in tire A. The results of this analysis are given in Table IV, under Tire A and Tire B.

As shown in the first part of each tabulation, the measured temperatures at the inner and outer walls of the tires can be matched by several combinations of strain amplitude and shear strain. However, as shown in the second part of each tabulation, strain amplitude — shear strain combinations which give a best match for tire A do not match the measured temperatures of tire B, except at a single unique combination of strain amplitude (1%) and shear strain (15%), for which the calculated temperatures match the measured temperatures in both the tires. (This unique combination is marked with an asterisk in Table IV.)

given average tension and cycling frequency, chosen to correspond to inflation pressure and speed of tire, respectively.

Temperatures are measured by thermocouples embedded at the chosen location, near to but not in the reinforced zone, while the tire is being rolled on a test wheel at given loading and speed.

Heat generation rates are measured on cords pulled from the tire after it has been run on the test wheel. These cords are tested over a range of strain amplitudes from about 0.5 to 1.15% and a temperature range from about 40° to 160°C. The heat generation rates are calculated from the stress-strain hysteresis loop experimentally found upon cyclic straining of the cords at given amplitude, temperature, frequency, and average tension ("pretension") in a device for measuring stress vs. strain. (A preliminary period of cyclic straining should be allowed, to effect the conditioning necessary for consistent results.)

A typical set of values of heat generation rate, for PET cord measured at average tension of about 2.5 Kg and frequency of 10 cps, are given in Table V below as a function of temperature and strain.

The procedure used for the evaluation of cord and rubber strain amplitudes in the tire side wall is similar to the one described in Example II above. The physical properties are as shown in that Example.

In the first step, a series of values for the strain amplitude of cords in the reinforced zone of the side wall is chosen. Similarly, a series of values is assigned for rub-

TABLE IV

| TIRE A Strain Amplitude (Cord=Rubber) (%) | Shear Strain (Rubber) (%) | BEST FIT | | | | Shear Strain (Rubber) Giving Best Fit For Tire B (%) | Inner Wall Calcd. (°C) | Outer Wall Calcd. (°C) |
|---|---|---|---|---|---|---|---|---|
| | | Inner Wall | | Outer Wall | | | | |
| | | Msd. (°C) | Calcd. (°C) | Msd. (°C) | Calcd. (°C) | | | |
| 0.6 | 50 | 85 | 85 | 71 | 71 | 38 | 77 | 65.5 |
| 0.8 | 32 | | 85 | | 71 | 24 | 79 | 66.5 |
| *1.0 | 15 | | 85 | | 71 | 15 | 85 | 71 |
| 1.2) | NO FIT POSSIBLE AT | | | | | NO FIT POSSIBLE AT | | |
| | THESE | | | | | THESE | | |
| 1.4) | CORD STRAINS | | | | | CORD STRAINS | | |
| TIRE B | | | | | | Best Fit for Tire A | | |
| 0.6 | 38 | 95.5 | 95 | 79 | 78.5 | 50 | 116 | 94 |
| 0/8 | 24 | | 96 | | 79 | 32 | 107 | 87 |
| *1.0 | 15 | | 95.5 | | 79 | 15 | 95.5 | 79 |
| 1.2) | NO FIT POSSIBLE AT | | | | | NO FIT POSSIBLE AT | | |
| | THESE | | | | | THESE | | |
| 1.4) | CORD STRAINS | | | | | CORD STRAINS | | |

EXAMPLE III

This example illustrates our invention applied to determine the cord and rubber layer strain amplitudes in the side wall of a vehicular pneumatic tire under rolling conditions. The values of strain amplitudes corresponding to a given loading and speed of the tire are obtained by our method, using the following parameters:

1. measured temperatures of the cord-reinforced zone and in the outer rubber layer, and the measured inside air temperature
2. ambient air temperature
3. construction geometry of the side wall
4. the physical properties of the cord and the rubber, and the volume fraction of cord in the cord-reinforced zone
5. rubber to air heat transfer coefficient
6. experimentally determined values of heat generation rate of the various tire constituents as a function of temperature and strain amplitude, and at ber strain amplitudes. The rubber strain amplitude in the cord-rubber composite zone is taken to be equal to the cord strain amplitude in that zone; and that in the rubber layer outside the composite zone is assumed to increase linearly through the rubber layer from the value in the composite zone to a maximum value at the outer surface. Since rubber shows linear viscoelastic behavior, the resulting average strain amplitude will represent the behavior of this entire rubber layer. (In this Example, the interply rubber shear strain, discussed in Example II, is not separately considered; and therefore the resulting heat generation, to the extent it exceeds that of the rubber surrounding the cords, is included in the heat generation due to the cords when determining strain amplitude of the cords.)

Each of the cord strain amplitude values chosen is combined with the several assigned values of the maximum rubber strain amplitude. The resulting temperature profiles across the side wall thickness are calculated by finite difference approximation of the heat exchange equation, $$\rho C_p (\partial T/\partial t) = K(\partial^2 T/\partial x^2) + Q_c V_c + Q_R(1-V_c)$$
where the symbols have the meanings shown in Example II, $x$ is the thickness dimension, and $c$ and $R$ refer to cord and rubber, respectively. The cord and rubber strain amplitude combination which gives a best match between the calculated temperature profile and the measured temperatures then defines the cord and maximum rubber strain amplitude operative during the rolling of the tire at the given speed and load.

The results of Table VI(A) below illustrate a typical case in which the temperature profile through the side wall of a radial passenger tire having PET cords is analyzed. The tire is tested at 50 mph and a load of 2046 lbs. The temperature at the inner side of the cord-reinforced zone and the temperature in the rubber layer close to the carcass, measured by thermocouples were 66.1°C and 61.4°C, respectively.

Cord strains were chosen in the range from 1.1 to 1.5% and maximum rubber strains in the range of 10.0 to 1.0%. Illustrative results of the calculation for the various combinations are shown in Table VI (A) below. The best combination, marked with an asterisk in Table VI(A) is that at which the calculated temperatures match the measured temperatures, at a cord strain amplitude of 1.09% and outer surface rubber strain amplitude of 5.0%. For the calculation the heat flow, as in Example II above, was assumed to be normal to the side wall surface; and the side wall was assumed to be a flat slab, i.e., the heat flow was assumed to be only along one rectangular coordinate (the thickness dimension).

The same procedure was followed to determine the strain amplitudes operative at other loads and speeds. The results obtained are summarized in Tables VI (B), (C) and (D) below.

TABLE V

Heat Generation Rates of a PET Tire Cord
(Average tension=2.5 Kg, frequency=10cps)

| Temperature °C | Heat Generation Rate (ergs/cm/sec) At Cord Strain Amplitude of | | |
|---|---|---|---|
| | 0.61% | 0.89% | 1.14% |
| 50 | $0.47 \times 10^4$ | $1.21 \times 10^4$ | $2.26 \times 10^4$ |
| 70 | 0.48 | 1.31 | 2.88 |
| 85 | 0.51 | 1.44 | 3.16 |
| 100 | 0.61 | 1.71 | 3.57 |
| 115 | 0.74 | 2.04 | 4.04 |
| 130 | 0.84 | 2.21 | 4.27 |
| 145 | 0.80 | 2.06 | 3.86 |
| 160 | 0.66 | 1.62 | 3.10 |

TABLE VI

Cord and Rubber Layer Strain Amplutudes in Radial PET Tires
((A) Speed = 50 mph    Load = 2046 lbs.)

| Strain Amplitudes Cord % | Rubber % (max) | Inside Temp Measured | Wall °C Calculated | Outside Temp Measured | Wall °C Calculated |
|---|---|---|---|---|---|
| 1.05 | 8.5 | 66.1 | 66.0 | 61.4 | 61.7 |
| *1.09 | 5.0 | '' | 66.1 | '' | 61.4 |
| 1.10 | 3.0 | '' | 65.9 | '' | 61.1 |
| 1.11 | 1.0 | '' | 66.1 | '' | 61.2 |

TABLE VI ((B) Speed=30 mph, various loads)

| Load on Tire lbs | Strain Amplitudes Cord % | Rubber %(max) | Inside Air Temp. °C | Inside Temp. Measd | Wall °C Calcd | Outside Temp Measd | Wall °C Calcd |
|---|---|---|---|---|---|---|---|
| 1580 | 1.09 | 4.5 | 57.2 | 53.9 | 53.9 | 51.4 | 51.4 |
| 1860 | 1.15 | 5.5 | 62.8 | 59.4 | 59.3 | 56.4 | 56.4 |
| 2046 | 1.15 | 5.0 | 66.1 | 60.6 | 60.5 | 57.1 | 57.2 |
| 2232 | 1.19 | 5.0 | 67.2 | 62.2 | 62.4 | 58.8 | 58.7 |

TABLE VI ((C) Speed=50 mph, various loads)

| Load on Tire lbs | Strain Amplitudes Cord % | Rubber %(max) | Inside Air Temp. °C | Inside Temp. Measd | Wall °C Calcd | Outside Temp Measd | Wall °C Calcd |
|---|---|---|---|---|---|---|---|
| 1580 | 1.03 | 5.4 | 66.1 | 59.4 | 59.4 | 55.7 | 55.6 |
| 1860 | 1.05 | 5.0 | 72.2 | 63.3 | 63.1 | 58.7 | 58.8 |
| 2046 | 1.09 | 5.0 | 75.0 | 66.1 | 66.1 | 61.4 | 61.4 |
| 2232 | 1.11 | 5.2 | 80.0 | 69.4 | 69.5 | 64.4 | 64.4 |

TABLE VI ((D) Speed=65 mph, various loads)

| Load on Tire lbs | Strain Amplitudes Cord % | Rubber %(max) | Inside Air Temp. °C | Inside Temp. Measd | Wall °C Calcd | Outside Temp Measd | Wall °C Calcd |
|---|---|---|---|---|---|---|---|
| 1580 | 0.99 | 4.9 | 72.2 | 62.2 | 62.2 | 57.6 | 57.6 |
| 1860 | 1.02 | 5.1 | 80.6 | 67.8 | 67.6 | 62.3 | 62.4 |
| 2046 | 1.06 | 6.0 | 83.9 | 71.7 | 71.6 | 65.7 | 65.8 |
| 2232 | 1.06 | 5.5 | 88.9 | 73.3 | 73.3 | 67.1 | 67.0 |

EXAMPLE IV

In this example, we show analyzing the tire temperature profile at the crown and shoulder region. Main difference between this region and the sidewall region which was discussed in Example III is that the one-dimensional approximation in the dynamic modelling which was good for the sidewall region is inadequate. The thickness of the tire wall varies significantly from position to position and the presence of grooves brings additional irregularity to the geometry.

Thus, the irregularity of the shapes of boundary surfaces makes the numerical simulation of the change of tire temperature profiles during the running of tires under a load much more complex in the crown and shoulder than for the sidewall.

In the sidewall, the boundary conditions applicable at the boundary surfaces are of the so-called von Neumann type in which the boundary conditions specify the rate of flux across the boundary surface. For example, at the exterior surface of sidewall, the boundary condition is $$-K_R (\partial T/\partial x) = h(T - T_a)$$

where $K_R$ is the thermal conductivity of rubber, $x$ is the position coordinate and $h$ is the heat transfer coefficient for heat transfer from the rubber to air (outside). The left hand side represents the heat flux at the interior side of the wall and the right hand side represents the heat flux at the outer side of the wall. The boundary condition means that the two fluxes are equal.

For an irregularly shaped boundary surface, application of boundary conditions of this type in the numerical simulation involves a complex procedure (See Sec. 20.10, p. 202 of Forsythe & Wasow - "Finite Difference Methods for Partial Differential Equations", John Wiley & Sons, Inc., New York (1960)). On the other hand, the boundary conditions of the so-called Dirichlet type, which specifies the values of the dependent variables at the boundary point, are much easier to handle (see Sec. 20.9, p. 198 of the same reference shown above) in the numerical simulation of the change of tire temperature profiled through crown and shoulder. For example, this type of boundary condition would specify the values of temperature $T_W$ at the outer side of the sidewall.

In order to avoid the complexities in analysis due to the von Neumann type boundary conditions on irregularly shaped boundary surfaces, we divide the crown and the shoulder region into three separate zones as shown in FIG. 4 so that the irregular boundary surfaces become regular ones.

Thus, the inner zone surrounded by the solid line is represented by a polar coordinate system ($r$ and $\theta$) and the inner wall is then represented as a circular curve of radius R. The crown zone and shoulder zone are represented by rectangular coordinate systems ($x$, $y$) and then the outside surfaces and groove surfaces are represented as straight regular boundary lines.

Note that we let the three regions have the overlapping zones (indicated by the cross-shading) at the borders between them. Purpose of having these overlapping zones is to facilitate the application of Dirichlet type boundary conditions for iterative matching of the temperature at the boundary zones. This will be elaborated on further in the subsequent paragraphs.

Referring to FIG. 4, the heat transfer equation for the three zones are as follows:

INNER ZONE $$\rho C_p\, \partial T/\partial t = K \left[\frac{1}{r} \partial/\partial r(r \partial T/\partial r) + \frac{1}{r^2} \partial^2 T/\partial \theta^2\right] + Q_c V_c + Q_R(1-V_c)$$

CROWN ZONE AND SHOULDER ZONE $$\rho C_p\, \partial T/\partial t = K[\partial^2 T/\partial x^2 + \partial^2 T/\partial y^2] + Q_c V_c + Q_R(1-V_c) \quad (2)$$

The symbols have their previous significance.

Initial conditions are:
$$T(r, \theta) = T_o$$
$$T(x, y) = T_o \quad (3)$$

The boundary conditions at the inner surface which is in contact with the inside air is given by a von Neumann type condition, i.e.

$$K(\partial T/\partial r) = h(T - T_a) \quad (4)$$

where K is the thermal conductivity of the wall material, $h_i$ is the heat transfer coefficient at the inner wall, and $T_a$ is the measured inside air temperature under steady state conditions of testing.

At the crown surface and shoulder surface which is in contact with the outside air, the boundary conditions are given by $$K_R\, \partial T/\partial y = h(T - T_a) \quad (5)$$

where $K_R$ is thermal conductivity of rubber, $T_a$ is ambient air temperature, and $h$ is heat transfer coefficient of rubber to air.

At the boundary line where the shoulder zone meets the sidewall, and at the boundary line where the right hand half of the inner zone and crown zone meet the left hand half of these zones, the boundary conditions based on the no flux criterion are:

$$(\partial T/\partial x) = 0$$

and $$(\partial T/\partial \theta) = 0$$

In the overlapping boundary regions between the three regions, the previously mentioned Dirichlet type boundary conditions are applied with iterations. At the time t, we assume that the boundary temperature of the inner region is that temperature in the neighboring regions (i.e., crown region and shoulder region) and proceed to apply Dirichlet type boundary conditions in solving the temperature profile of the inner region. After that, we go to the crown region or shoulder region and use the corrected values of temperature of the inner region as the basis for establishing a new boundary temperature for the region, This iterative procedure is repeated until the calculated boundary temperature does not change.

The heat transfer equations (1) and (2) are solved through finite difference approximation via the "implicit alternating direction method" (see e.g. Sec. 22.4, p. 272 of Forsythe and Wason, cited previously).

In making the calculation the cord strain amplitudes in the shoulder composite region are taken to be equal to the cord strain amplitudes in the sidewall composite region of the same tire and for the same load and speed. As in the case of sidewall, Ex. III, the cord strain amplitude in the shoulder is combined with several values for the rubber strain amplitude. Moreover, we treat the rubber strain amplitude at the composite region as equal to the cord strain amplitude at that region.

The rubber strain amplitude in the outer rubber layer is assumed to be different from that in the composite region and constant over the entire thickness of the shoulder region. This is in contrast to the sidewall case, described in Example III, where the rubber strain amplitude was taken as increasing to a maximum value at the outermost rubber surface. The reason for this is the difference in the mode of deformation of rubber at the two regions. Whereas in the sidewall the predominant rubber deformation mode is flexing so that outer layers are subjected to progressively higher strains, in the shoulder region, the principal deformation mode is compression. Therefore, in the shoulder region we believe that the assumption of equal strain amplitude over the whole thickness of the rubber layer is closer to the real case than a linear gradient as assumed for the sidewall.

The combination of cord strain amplitude (based on that in the sidewall) and constant rubber strain amplitude which best matches the calculated temperature to be measured temperature at the inside of the shoulder, then defines the rubber strain amplitude in the shoulder. The results in Tables VII(A) and VII(B) show that these rubber strains giving the best match vary from about 10–20% depending on the load and the speed.

TABLE VII (A) PET Light Truck Tire
Shoulder Strain Amplitudes

| Speed mph | Load on Tire lbs | Strain Amplitudes % Cord | Strain Amplitudes % Rubber | Inner Shoulder Temp °C Measd | Inner Shoulder Temp °C Calcd | Measured Inside Air Temp °C (Steady State) |
|---|---|---|---|---|---|---|
| 35 | 1770 | 0.60 | 12.3 | 87.8 | 87.7 | 77.8 |
|  | 2060 | 0.63 | 14.4 | 93.9 | 93.9 | 83.9 |
|  | 2190 | 0.70 | 16.2 | 101.7 | 101.5 | 86.1 |
|  | 2310 | 0.72 | 16.4 | 104.0 | 104.1 | 90.5 |
| 50 | 1770 | 0.62 | 12.0 | 95.0 | 95.1 | 86.1 |
|  | 2060 | 0.65 | 14.6 | 110.0 | 110.2 | 93.8 |
|  | 2190 | 0.65 | 16.3 | 118.2 | 118.0 | 97.4 |
|  | 2310 | 0.69 | 16.8 | 123.2 | 123.4 | 101.1 |
| 65 | 1770 | 0.58 | 13.3 | 109.4 | 109.2 | 96.1 |
|  | 2060 | 0.58 | 16.5 | 129.2 | 129.0 | 105.7 |
|  | 2190 | 0.62 | 17.7 | 136.4 | 136.6 | 110.0 |
|  | 2310 | 0.65 | 18.5 | 141.9 | 141.5 | 115.4 |

TABLE VII (B) PET Light Truck Tire
Shoulder Strain Amplitudes

| Speed mph | Load on Tire lbs | Strain Amplitudes % Cord | Strain Amplitudes % Rubber | Inner Shoulder Temp °C Measd | Inner Shoulder Temp °C Calcd | Measured Inside Air Temp °C (Steady State) |
|---|---|---|---|---|---|---|
| 35 | 1770 | 0.57 | 15.0 | 90.0 | 90.1 | 75.6 |
|  | 2060 | 0.78 | 16.8 | 100.6 | 100.4 | 83.9 |
|  | 2190 | 0.82 | 17.3 | 103.3 | 103.0 | 86.1 |
|  | 2310 | 0.88 | 18.0 | 107.3 | 107.1 | 89.4 |
| 50 | 1770 | 0.62 | 14.0 | 98.3 | 98.5 | 86.7 |
|  | 2060 | 0.82 | 16.7 | 113.3 | 113.5 | 92.8 |
|  | 2190 | 0.84 | 17.7 | 119.3 | 119.0 | 97.2 |
|  | 2310 | 0.86 | 17.4 | 121.0 | 121.2 | 100.0 |
| 65 | 1770 | 0.60 | 13.9 | 111.1 | 111.0 | 95.6 |
|  | 2060 | 0.78 | 16.0 | 124.3 | 124.0 | 104.0 |
|  | 2190 | 0.81 | 16.5 | 129.2 | 129.5 | 107.3 |
|  | 2310 | 0.82 | 16.8 | 135.3 | 135.1 | 111.7 |

We claim:

1. Method of determining the strain amplitudes of the two principal components of a structure composed principally of two viscoelastic materials A and B at least one of which shows non-linear viscoelastic behavior under strain, due to cyclic straining of the structure with heat generation, comprising the following steps:

1. Experimentally determining rates of heat generation, Q, per unit volume of each material, due to cyclic straining, for each material at a series of temperatures by hysteresis measurements at various strain amplitudes ($\epsilon_A$) for material (A) and ($\epsilon_A$) for material (A) and ($\epsilon_B$) for material (B);

2. Calculating by computer for each pair of a set of pairs of strain amplitudes ($\epsilon_A$, $\epsilon_B$), the steady-state temperatures at two positions (P) and (P') in the structure, using finite difference approximations at successive positions through the structure, to solve the heat balance equation appropriate for the particular structure, having as its simplest form:

$$\sigma C_p\, \partial T/\partial t = K\, \partial^2 T/\partial q^2 + Q$$

where $\partial/\partial t$ indicates partial differentiation by time; $\partial/\partial q$ indicates partial differentiation by the space coordinate;

$\sigma$ = density
$C_p$ = heat capacity per unit volume
$T$ = temperature
$K$ = coefficient of thermal conductivity
$Q$ = heat generation rate per unit volume, at the temperature calculated for each volume element dV and at the value of strain amplitude ($\epsilon_A$) or ($\epsilon_B$) imposed upon the material (A) or (B);

3. Representing the calculated set of temperatures at (P) as a function of strain amplitudes, $\epsilon$, of one of the materials for each value of the other $\epsilon$, and likewise representing the calculated set of temperatures at (P');

4. Experimentally determining steady-state temperatures $T_P$ and $T_P'$ at positions (P) and (P') of the structure as it undergoes the specified straining cycle;

5. Representing the curve of $\epsilon_A$ vs. $\epsilon_B$ at the temperature $T_P$ and an likewise the $\epsilon_A$ vs. $\epsilon_B$ curve at the temperature $T_P'$ using the data revealed by step (3) above;

6. Observing the intersections of the two curves revealed by step (5) above, thereby determining a pair of strain amplitudes ($\epsilon_A$, $\epsilon_B$) imposed by the cyclic straining, which pair of amplitudes will give rise to the experimentally determined temperatures $T_P$ and $T_P'$.

2. Method of claim 1 wherein said structure is the side wall of a vehicular pneumatic tire composed principally of material showing linear viscoelastic behavior under strain, and of reinforcing material.

3. Method of determining the strain amplitudes for each of the two constituent materials of a structure in accordance with claim 1, wherein more than one pair of strain amplitudes ($\epsilon_A$, $\epsilon_B$) corresponds to an intersection of the curves determined at step (5) of claim 1, which method comprises determining such curves for two such structures having a difference in heat generation rates of one of their components but being otherwise closely similar; and observing the intersection which applies to both structures.

4. Method of claim 3 wherein said structure is the sidewall of a vehicular pneumatic tire composed of a reinforced zone of plies of material showing non-viscoelastic behavior embedded in rubber and separated by interply rubber layers, the whole being between an inner and an outer layer of rubber.

5. Method of claim 1 wherein said structure is the shoulder region of a vehicular pneumatic tire composed principally of material showing linear viscoelastic behavior under strain, and of reinforcing material.

* * * * *

UNITED STATES PATENT AND TRADEMARK OFFICE
CERTIFICATE OF CORRECTION

PATENT NO. : 3,934,452
DATED : January 27, 1976
INVENTOR(S) : Dusan C. Prevorsek, Young D. Kwon and Raj K. Sharma It is certified that error appears in the above–identified patent and that said Letters Patent are hereby corrected as shown below:

Col. 2, line 1, "indicated" should be -- indicate --.

Col. 3, line 49, "s" should be -- a --.

Col. 4, line 13, "conducivity" should be -- conductivity --.

lines 58 and 62, the symbols "∂" should be on the line, not superscripts.

Col. 6, line 17, the word -- effective -- and the symbol -- $\varepsilon$ -- should be in quotes.

line 19, the word -- recorded -- should be in quotes.

line 22, the word -- effective -- should be in quotes.

line 53, the word -- effective -- should be in quotes.

Col. 7, line 55, "$(\varepsilon_c, \varepsilon)$" should be -- $(\varepsilon_c, \varepsilon_w)$ --.

line 63, "respectivley" should be -- respectively --.

Col. 9, line 5, "$T_p$" second occurrence, should be -- $T_p'$ --.

line 11, "FIG. s(b)" should be -- FIG. 5(b) --.

line 13, "$T_p$" should be -- $T_p'$ --.

line 19, "5(C)" should be -- 5(c) --.

line 21, "$T_p = 65.5°$" should be -- $T_p' = 65.5°$ --.

UNITED STATES PATENT AND TRADEMARK OFFICE
CERTIFICATE OF CORRECTION

PATENT NO. : 3,934,452
DATED : January 27, 1976
INVENTOR(S) : Dusan C. Prevorsek, Young D. Kwon and Raj K. Sharma It is certified that error appears in the above-identified patent and that said Letters Patent are hereby corrected as shown below:

Col. 9, line 24, "5(C)" should be -- 5(c) --.

line 51, after the word "strain" insert -- of --.

Col. 10, line 7, in the formula, after that portion which reads "$(\partial T/\partial x)_R$" insert -- = --.

line 15, the terms -- R -- and -- m -- should be in quotes.

in the table, second line, third column, "11.15" should be -- 1.15 --.

Col. 11, Table IV, first column, second entry under "TIRE B", "0/8" should be -- 0.8 --.

Col. 12, line 5, "location" should be -- locations --.

Col. 13, line 2, the term -- x -- should be in quotes.

line 3, the terms -- c -- and -- R -- should be in quotes.

line 18, "1.1" should be -- 1.05 --.

line 19, "1.5%" should be -- 1.15% --.

UNITED STATES PATENT AND TRADEMARK OFFICE
CERTIFICATE OF CORRECTION

PATENT NO. : 3,934,452
DATED : January 27, 1976
INVENTOR(S) : Dusan C. Prevorsek, Young D. Kwon and Raj K. Sharma It is certified that error appears in the above-identified patent and that said Letters Patent are hereby corrected as shown below:

Col. 14, Table VI, in all four parts, the headings of the four right hand columns should read:

-- Inside Wall
    Temp. °C
  Measd  Calcd -- and

-- Outside Wall
    Temp. °C
  Measd  Calcd --

Col. 15, line 32, the terms -- $K_R$ -- and -- x -- should be in quotes.

line 33, the term -- h -- should be in quotes.

line 42, "Wasow" should be -- Wason --.

line 60, -- inner zone -- should be in quotes.

line 64, -- crown zone -- and -- shoulder zone -- should be in quotes.

Col. 16, line 22, in the formula, "I" should be -- T --.

Claim 1, col. 18, lines 8 and 9, delete "and ($\epsilon_A$) for material (A)".

UNITED STATES PATENT AND TRADEMARK OFFICE
CERTIFICATE OF CORRECTION

PATENT NO. : 3,934,452
DATED : January 27, 1976
INVENTOR(S) : Dusan C. Prevorsek, Young D. Kwon and Raj K. Sharma It is certified that error appears in the above–identified patent and that said Letters Patent are hereby corrected as shown below:

Claim 1, col. 18, line 17, in the formula, "$\sigma$" should be -- $\rho$ --.

line 21, "$\sigma$" should be -- $\rho$ --.

next to last line, the symbol -- $\varepsilon$ -- should be in quotes.

Signed and Sealed this eighteenth Day of May 1976

[SEAL]

Attest:

RUTH C. MASON
Attesting Officer

C. MARSHALL DANN
Commissioner of Patents and Trademarks